United States Patent [19]
Crow et al.

[11] Patent Number: 6,117,642
[45] Date of Patent: Sep. 12, 2000

[54] METHODS OF DETERMINING DISEASE ACTIVITY IN SLE PATIENTS BY CORRELATING THE LEVEL OF SOLUBLE CD40 LIGAND

[75] Inventors: Mary K. Crow; Radha Krishna Vakkalanka, both of New York, N.Y.

[73] Assignee: New York Society for the Relief of the Ruptured and Crippled Maintaining the Hospital for Special Surgery, New York, N.Y.

[21] Appl. No.: 08/966,123

[22] Filed: Nov. 7, 1997

Related U.S. Application Data

[60] Provisional application No. 60/029,719, Nov. 8, 1996.

[51] Int. Cl.⁷ .......................... G01N 33/53; G01N 33/536
[52] U.S. Cl. .......................... 435/7.1; 436/501; 436/506; 436/536
[58] Field of Search .............................. 435/7.1; 436/501, 436/506

[56] References Cited

U.S. PATENT DOCUMENTS 5,292,636  3/1994  Kung et al. .

OTHER PUBLICATIONS

Graf et al. Eur. J. Immunol. 25: 1749–1754 (1995).

Koshy et al. J. Clin Invest. 98: 826–837 (1996).

Desai–Mehta et al. Arthritis & Rheumatism 38 (9 Suppl.) p. S314 (1995).

Koshy et al. et al. Arthritis & Rheumatism 38 (9 Suppl) p. S156 (1995).

Vakkalanka et al., *Arthritis & Rheumatism*, 39(9):S35 abstract 52, 1996.

MacDonald et al., *Arthritis & Rheumatism*, 39(9):s159, abstract 793, 1996.

*Primary Examiner*—Phillip Gambel
*Attorney, Agent, or Firm*—Darby & Darby

[57] ABSTRACT

The present invention provides diagnostic methods for determining the severity of disease or disease activity in patients suffering from autoimmune, inflammatory, malignant, vascular, or viral diseases, which involves measuring the level of CD40 ligand (CD40L) in the patient's serum or other body fluid.

3 Claims, 22 Drawing Sheets

FIG. 8A

| SUBJECT GROUP | MEAN SOLUBLE CD40 LIGAND (ng/ml) |
|---|---|
| Normal Subjects (n = 22) | 0.23 + 0.14 |
| SLE Patients (n = 60) | 9.13 + 6.26 |
| Disease Control Subjects (n = 30) | 2.71 + 3.16 |
| - Rheumatoid Arthritis (n = 9) | 2.26 + 3.93 |
| - Wegener's Granulomatosis (n = 7) | 3.17 + 2.71 |
| - Antiphospholipid Antibody Syndrome (n = 6) | 7.92 + 5.56 |
| - Others (n = 14) | 2.76 + 3.04 |

FIG. 8B

| DISEASE SEVERITY OF SLE PATIENTS | MEAN SOLUBLE CD40 LIGAND (ng/ml) |
|---|---|
| Severe (nephritis and/or central nervous system) | 12.09 + 6.94 |
| Moderate (mild/moderate proteinuria or low C') | 7.93 + 3.86 |
| Mild (no clinical organ involvement) | 5.28 + 3.90 |

FIG. 8C

| Serum CD40L in patients with APL and a history of arterial thrombosis or evidence of atherosclerosis on carotid doppler (ng/ml) | Serum CD40L in patients with APL and no history of arterial thrombosis and no evidence of atherosclerosis on carotid doppler (ng/ml) |
|---|---|
| 11.9 | 3.9 |
| 7.7 | 3.9 |
| 12.0 | 0.7 |
| 12.1 | - |
| 14.3 | - |

Medium

293-CD40L

293-CD8

METHODS OF DETERMINING DISEASE ACTIVITY IN SLE PATIENTS BY CORRELATING THE LEVEL OF SOLUBLE CD40 LIGAND

This application claims priority pursuant to 35 U.S.C. §119 from Provisional Application Serial No. 60/029,719 filed Nov. 8, 1996, the entire disclosure of which is hereby incorporated by reference.

FIELD OF THE INVENTION

This invention pertains to methods for assessing autoimmune, inflammatory, malignant or vascular disease activity in humans, including methods for assessing response to immunosuppressive therapies.

BACKGROUND OF THE INVENTION

The activation of B cells and their differentiation into antibody secreting cells is triggered by antigen and requires T helper (Th) cells. Not only do Th cells control activation of B cells, they also control isotype switching (IgM to IgG) and initiate somatic hypermutation. (Janeway et al., *Immunobiology*, Garland Publishing, New York, 1997). Th cells also play an important role in activating macrophages and in coordinating the response of the host to intracellular pathogens.

The proteins most responsible for controlling the interaction between Th cells and various target cells are CD40 and CD40 ligand (CD40L). Interaction of membrane-bound CD40 and CD40L triggers B-cell activation. Preventing formation of the CD40-CD40L complex (as with, e.g., monoclonal antibodies) has been shown to inhibit (i) murine AIDS-associated splenomegaly, hypergammaglobulinemia, and immunodeficiency in disease susceptible mice (Green et al. *J. Virol.* 70:2569, 1996); (ii) insulinitis and diabetes in nonobese diabetic mice (Balasa et al. *J. Immunol.* 159:4620, 1997); (iii) murine thyroiditis (Carayanniotis et al. *Immunology* 90:421, 1997); (iv) CD4+ T cell mediated alloreactivity after bone marrow transplantation (Blazar et al., *J. Immunol.* 158:29, 1997); (v) the immune response to infection with recombinant adenovirus (Kay et al., *Proc. Natl. Acad. Sci. U.S.A.* 94:4686, 1997); (vi) allograft rejection of transplanted skin or cardiac tissue (Larsen et al. *Nature* 381:434, 1996); (vii) murine membranous glomerulonephritis (Biancone et al. *Kidney Intl.* 48:458, 1995); and (viii) lupus-nephritis in a murine model of systemic lupus erythematosus (Early et al. *J. Immunol.* 157:3159, 1996). Thus, it is clear that the interaction CD40 and CD40L plays an important role in normal and pathological immune system function.

CD40L is expressed in T cells., activated B cells, a subpopulation of blood dendritic cells, smooth muscle cells, and vascular endothelial cells and, importantly, is present as a soluble form in the blood (Grammar et. al., *J. Immunol.* 154:4996, 1995; Blossom et. al., *J. Immunol.* 159:4580, 1997; Pinchuk et. al., *J. Immunol.* 157:4363, 1996; and, Mach et. al., *Proc. Natl. Acad. Sci. U.S.A.* 94: 1931, 1997). Furthermore, the present inventors have found that CD40L is expressed in malignant cells, including, for example B cell malignancies such as chronic lymphocytic leukemia (CLL). The expression of CD40L on endothelial cells and smooth muscle cells also suggests that this protein plays an important role in the induction of vascular damage, as is observed, for example, in athersclerosis or thrombosis (Mach et al., *Proc. Natl. Acad. Sci. U.S.A.* 94:1931, 1997). Because of the importance of CD40L in a wide range of diseases or disease processes, such as, e.g., inflammation, there is a need in the art for a reliable diagnostic and prognostic method to monitor disease activity and response to therapy, by assaying the expression or presence of CD40L.

CD40L is a 261-amino acid type II transmembrane protein. One or more biologically active soluble forms of the molecule, collectively designated sCD40L, are produced by proteolytic cleavage of the full-length form, which may occur intracellularly or on the cell surface. sCD40L is important in inflammation. For example, an sCD40L fusion protein (CD40L-CD8) induced a pulmonary inflammatory response in transgenic mice expressing the soluble protein. (Wiley et al. *J. Immunol.* 158:2932 (1997).

When a patient is diagnosed with an autoimmune disease such as sytemic lupus erythematosus (SLE), a B cell malignancy such as CLL, an inflammatory process, or a vascular disease such as atherosclerosis or thrombosis, the choice of appropriate therapeutic interventions would be considerably facilitated by diagnostic and prognostic indicators that accurately reflect the current severity of the disease, predict future severity, and monitor response to therapy. Thus, there is a need in the art for reliable diagnostic and prognostic methods to monitor disease activity and response to therapy in patients suffering from autoimmune disease.

SUMMARY OF THE INVENTION

The present invention encompasses methods for assessing the immune, inflammatory, or malignant status of human patients, which comprise measuring the levels of soluble CD40 ligand (sCD40L) in serum or other body fluids. Patients to which the methods of the invention may be applied include without limitation patients suffering from systemic autoimmunity or inflammation, vascular diseases, viral diseases, or malignancies, or patients undergoing immunosuppressive therapy.

In one aspect, the invention provides methods for monitoring autoimmune, inflammatory, malignant, or vascular disease activity in a patient, which are carried out by the steps of:

(a) establishing a statistically significant correlation between sCD40L levels in serum or other body fluids and the presence and/or severity of a particular autoimmune, inflammatory, malignant, viral, or vascular disease;

(b) measuring the sCD40L level in the patient's serum or other body fluid; and (c) determining whether the measured sCD40L level corresponds to a level correlated with the disease, and, if so, corresponds to a level correlated with mild or severe forms of the disease. In one set of embodiments, sCD40L levels are measured in a patient previously diagnosed as suffering from a particular autoimmune, malignant, vascular or inflammatory disease. In another embodiment, sCD40L levels are measured in a patient who has undergone an organ transplant or is otherwise at risk for graft versus host disease. In yet another embodiment, sCD40L levels are measured to detect previously undiagnosed autoimmune, malignant, viral, vascular or inflammatory disease activity in a patient.

Diseases to which the methods of the present invention can be applied include without limitation immune system diseases such as, e.g., systemic lupus erythematosus (SLE), Wegener's granulomatosis, polyarteritis nodosa, cryoglobulinemic vasculitis, Sjogren's syndrome, mixed connective tissue disease, glomerulonephritis; conditions of systemic inflammation such as may be present, e.g., in patients undergoing chronic hemodialysis; malignancies such as, e.g., B cell leukemias and lymphomas; and, vascular damage. Methods for measuring sCD40L include without limitation immunoassays, receptor-binding assays, and biological activity assays.

In another aspect, the invention provides methods for monitoring the efficacy of immunosuppressive therapy in a patient undergoing such therapy. The methods are carried out by the steps of:

(a) establishing a statistically significant correlation between sCD40L levels and clinical response, or lack thereof, to immunosuppressive therapy;

(b) measuring the sCD40L level in the patient; and, (c) determining the correspondence between the sCD40L level measured in the patient and the sCD40 levels correlated to response, or lack of response, to immunosuppressive therapy.

Immunosuppressive therapies to which the monitoring methods of the present invention can be applied include without limitation administration of: cyclosporin A; metalloproteinase inhibitors; any agent that alters the transcription or translation of CD40L, the enzymatic processing of the full length form of CD40L to the soluble, secreted form, or the clearance of sCD40L from body fluids; treatments that block the binding of CD40L to the cell surface, such as administration of soluble CD40L, monoclonal antibodies, small molecular inhibitors or soluble receptors; or treatments that ablate malignant cell populations expressing CD40L.

BRIEF DESCRIPTION OF THE DRAWINGS

FIG. 5B is a graphic illustration of a standard curve of an ELISA measuring purified, recombinant human CD40L.

FIG. 6B is a graphic illustration of CD40L levels as measured by ELISA in serum from a patient with SLE (upward triangles and circles) and a normal subject (downward triangles and squares). Serum samples were incubated for 16 h with increasing concentrations of anti-CD40L monoclonal antibody (circles and squares) or an irrelevant antibody (triangles) prior to the ELISA.

FIGS. 8A–C is a table documenting the mean concentration of soluble CD40L, measured by ELISA, in serum samples from normal subjects, SLE patients, and patients serving as disease controls.

FIG. 8B is a table showing the association between the concentration of soluble CD40L in serum and the severity of disease in patients with SLE.

FIG. 8C is a table showing the association between concentration of soluble CD40L and the presence of atherosclerosis or a history of artenal thrombosis in patients suffering from antiphospholipid antibody syndrome.

DETAILED DESCRIPTION OF THE INVENTION

Figure 1A:
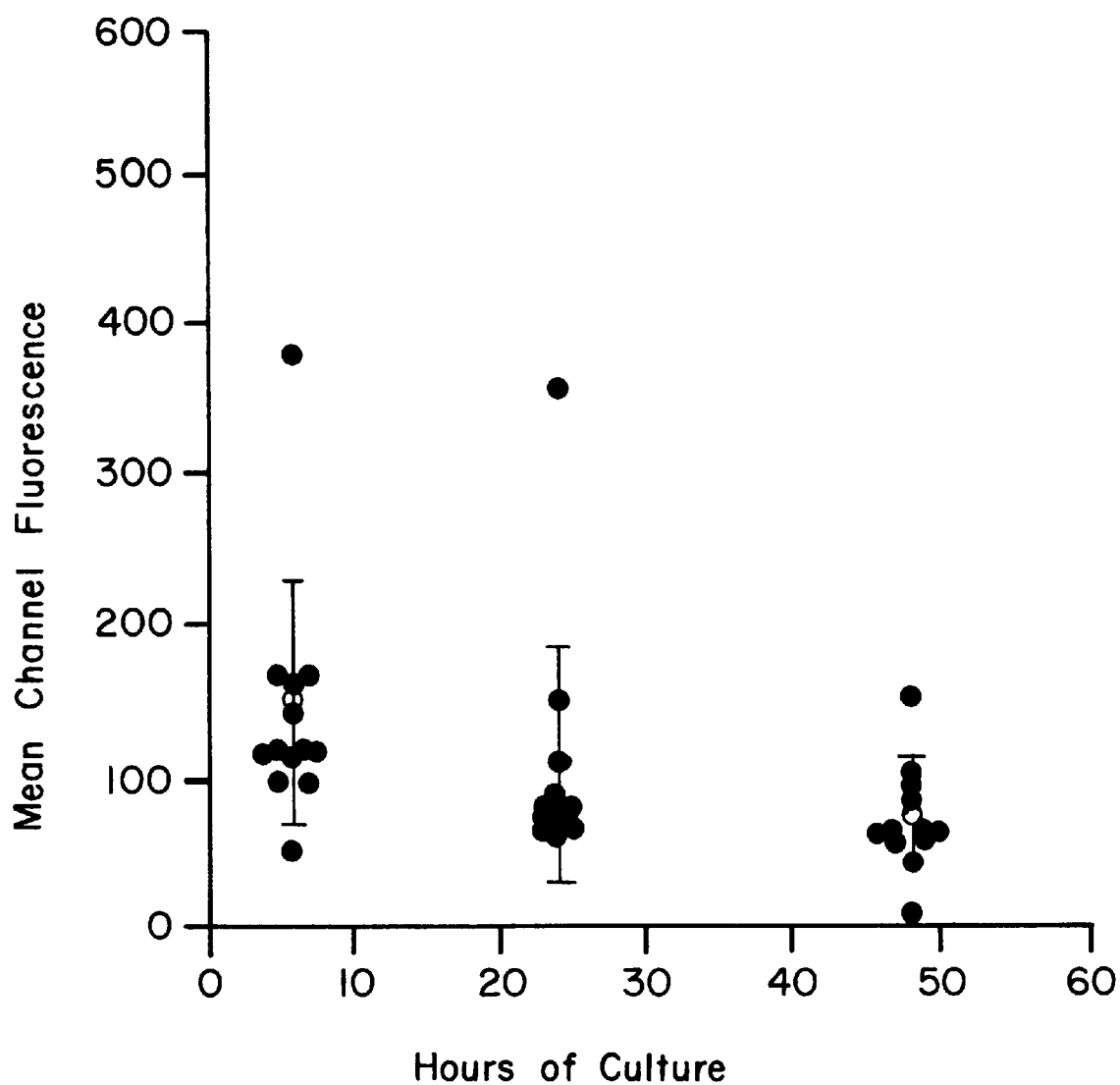
FIGS. 1A, 1B and 1C are histograms showing the kinetics of CD40L expression on peripheral blood mononuclear cells as a function of time after activation with the phorbol ester PMA and ionomycin. CD40L expression was measured by indirect immunfluorescence and flow cytometry, and the results are expressed as mean channel fluorescence (MCF) of the population of cells above the background fluorescence. CD40L expression was measured in normal subjects, SLE patients, and disease control patients.

All patent applications, patents, and literature references cited in this specification are hereby incorporated by reference in their entirety. In the case of inconsistencies, the present description, including definitions, will control.

The present invention is based on the present inventors' discovery that: (i) a soluble form of CD40L, designated sCD40L (Graf et al., *Eur. J. Immunol.* 25:1749, 1995; Pictravalle et al., *J. Biol. Chem.* 271:5965, 1996), can be detected in the serum of patients suffering from autoimmune diseases; and (ii) the levels of sCD40L measured in human serum reflect autoimmune disease activity. Furthermore, the present inventors have discovered that CD40L is expressed on the surface of malignant cells such as, e.g., B cell malignancies. According to the present invention, autoimmune, inflammatory, malignant, or vascular disease activity, as well as the efficacy of immunosuppressive therapies, can be monitored by measuring levels of sCD40L in one or more body fluids of a patient, preferably in serum. The measured levels are then compared with pre-determined sCD40L levels that have been shown to be correlated in a statistically significant fashion with disease activity or response to immunosuppressive therapies.

The present invention encompasses the establishment of such statistically significant correlations, where they exist. To achieve this, sCD40L levels in a large number of patients suffering from a particular autoimmune, inflammatory, malignant, or vascular disease are determined, and are compared with sCD40L levels in control (i.e., healthy) patients that have been matched for age, sex and ethnic origin. A statistical method such as a 2×3 Chi square test is then used to determine whether the sCD40L levels in the disease and normal groups are the same or different. In this manner, it is possible to obtain statistically significant correlations between a given pathological syndrome and sCD40L levels in one or more body fluids. Such correlations are believed to provide an important indicator of disease status and clinical outcome.

Diseases to which the methods can be applied include without limitation systemic lupus erythematosus (SLE), systemic vasculitides such as Wegener's granulomatosis, polyarteritis nodosa, and cryoglobulinemic vasculitis; Sjogren's syndrome; mixed connective tissue disease; graft-versus-host disease (including, e.g., the response of a host to bone marrow or cardiac transplantation); progressive systemic sclerosis or CREST syndrome; pseudogout; kidney diseases such as glomerulonephritis; systemic inflammatory conditions such as those suffered by patients on chronic hemodialysis; progressive systemic sclerosis; pseudogout; vascular disease, such as, e.g., atherosclerosis and arterial thrombosis, including without limitation that exhibited in patients with antiphospholipid antibody syndrome; malignancies of cells that express CD40L, such as CLL; and any acute or chronic viral infection that is characterized by T cell activation, such as, e.g., an infection caused by cytomegalovirus (CMV), human immunodeficiency virus (HIV), hepatitis virus (particularly hepatitis B or C), and herpesviruses.

The clinical manifestations of these diseases range from mild to severe. Mild disease encompasses symptoms that may be function-altering and/or comfort-altering, but are neither immediately organ-threatening nor life-threatening. Severe disease entails organ-threatening and/or life-threatening symptoms. For example, severe autoimmune disease is often associated with clinical manifestations such as nephritis, vasculitis, central nervous system disease, premature atherosclerosis or lung disease, or combinations thereof, that require aggressive treatment and may be associated with premature death. Anti-phospholipid antibody syndrome is often associated with arterial or venous thrombosis. Malignancies, such as CLL, are associated with immune system abnormalities such as autoantibody production. Any statistically significant correlation that is found to exist between serum sCD40L levels and any clinical parameters of an autoimmune, inflammatory, vascular, viral, or maligant disease would enable the use of a serum sCD40L assay as part of a diagnostic battery for that disease or group of diseases.

Diseases can exhibit ranges of activities. As used herein, disease activity refers to whether the pathological manifestations of the disease are fulminant, quiescent, or in a state between these two extremes. For example, a patient suffering from SLE having active disease would manifest a comparatively low level of serum complement, whereas a patient having inactive disease would manifest comparatively higher or normal level of serum complement. It will be understood that each of the diseases encompassed by the invention can be evaluated using known staging parameters well-known to those of ordinary skill in the art (Harrison's *Principles of Internal Medicine.*)

In practicing the present invention, sCD40L levels in an individual patient are measured in one or more body fluids, including without limitation plasma, serum, urine, saliva, synovial fluid, cerebrospinal fluid, and the like. sCD40L is measured using any appropriate method, including without limitation: immunoassays that measure sCD40L immunoreactive material; receptor binding assays that measure the interaction of sCD40L with CD40; and biological activity assays that measure a physiological consequence of CD40L-CD40interaction.

Immunoassays useful for measuring sCD40L include without limitation radioimmunoassays; ELISA; and Western blotting. The anti-sCD40L antibodies used in these assays may be polyclonal or monoclonal; the only requirement is that they bind sCD40L with sufficient affinity and specificity to enable the measurement of sCD40L in the particular assay conditions used. The antibodies may be used without purification, or may be purified by standard methods, as disclosed in, e.g., in *The Art of Antibody Purification*, 1989, Amicon Division, W.R. Grace & Co. Immunoassay methods are disclosed in, e.g., *Immunochemical Methods in Cell and Molecular Biology*, 1987 (Mayer and Waler, eds; Academic Press, London); and *Handbook of Experimental Immunology*, 1986, Volumes I–IV (Weir and Blackwell eds.) An example of an ELISA that measures sCD40L is described in detail in Example 3 below.

Receptor binding assays typically employ native CD40 and measure the ability of a sample to compete with radio-labelled sCD40L for binding to CD40. CD40 for use in the assay may be present on native B cells that display CD40 on their cell surface, or cells that have been programmed to express CD40 using recombinant DNA technology. Alternatively, the assay may employ purified CD40 isolated from a native or recombinant source. Fragments of CD40 that retain the capacity to bind sCD40L may also be used; such fragments may be derived from CD40 proteolytically or may result from expression of a truncated CD40 gene. In addition, variant forms of CD40L that retain CD40-binding capacity may be used. The nucleotide and amino acid sequence of CD40L is disclosed in Graf et al., *Eur. J. Immunol.* 22:3191, 1992; and Shimadzu et al., *Biochim. Biophys. Acta* 1260:67, 1995. Recombinant expression of wild-type and variant CD40L is disclosed in, e.g., Bajorath et al., *Biochemistry* 34:1833, 1995; and Bajorath et al., *Biochemistry* 34:9884, 1995. Techniques for recombinant expression and/or purification of full-length and truncated CD40 are well known and are explained fully in, e.g., Sambrook et al., 1989, *Molecular Cloning: A Laboratory Manual*, Second Edition, Cold Spring Harbor Laboratory Press, Cold Spring Harbor, N.Y.; *DNA Cloning: A Practical Approach*, Volumes I and II, 1985 (D.N. Glover ed.); and Scopes, 1987, *Protein Purification: Principles and Practice*, Second Edition (Springer-Verlag, N.Y.).

Biological activity assays for use in the present invention measure cellular responses to the functional interaction of sCD40L with CD40, including without limitation: stimulation of B-cell proliferation; induction of B-cell surface activation, adhesion, and co-stimulatory molecules, such as, for example, CD23, CD54, CD80, CD86, CD95 and MHC Class II; B-cell stimulation of allogeneic T-cell proliferation; antibody production; immunoglobulin class switching; stimulation of endothelial cells or fibroblasts to express adhesion molecules; and stimulation of macrophages or dendritic cells to express cell surface activation molecules or cytokines such as interleukin-12. Typically, the biological activity of a sample is measured before and after incubation with neutralizing amounts of anti-CD40L antibody, and the difference between the two measurements reflects sCD40L-mediated activity.

It will be understood that any statistically significant correlation between disease activity and sCD40L levels that is established using a particular sCD40L assay technique can be extended to sCD40L levels measured using an alternative technique. This is achieved, for example, by establishing a secondary correlation between sCD40L levels measured using an ELISA or radioimmunoassay and those measured using a receptor-binding or biological activity assay.

In a preferred embodiment, serum sCD40L levels are measured by ELISA using a mouse monoclonal antibody specific for human CD40L. Using this assay, serum sCD40L levels in normal subjects were found to be <200 pg/ml, while the levels in patients with active SLE ranged from about 5000 to about 30,000 pg/ml (See Example 4 below). Accordingly, the measurement of a serum sCD40L level greater than about 3 standard deviations above the mean of population of normal control subjects provides a useful diagnostic indicator of active SLE. Measurement of a serum sCD40L level between about 1–3 standard deviations above the mean of a population of normal subjects provides a useful diagnostic indicator of the presence of autoimmune disease in general, including inactive SLE, vasculitis, or other conditions of systemic inflammation. It was also found that serum sCD40L levels declined markedly following initiation of cyclosporin A treatment (see Example 7 below). Accordingly, the measurement of a decline in serum sCD40L levels provides a useful diagnostic indicator of clinical response to immunosuppressive therapy.

Immunosuppressive therapies to which the monitoring methods of the present invention can be applied include without limitation administration of: cyclosporin A; metalloproteinase inhibitors; any agent that alters the transcription or translation of CD40L, the enzymatic processing of the full length form of CD40L to the soluble, secreted form, or the clearance of sCD40L from body fluids; treatments that absorb or block the binding of CD40L to the cell surface, such as soluble CD40L, monoclonal antibodies, small molecular inhibitors or soluble receptors; or treatments that ablate malignant cell populations expressing CD40L.

The following working examples are intended to serve as non-limiting illustrations of the present invention.

EXAMPLE 1

Increased Expression of CD40L in Patients with Systemic Lupus Erythematosis (SLE)

The following experiments were performed to examine the level and kinetics of expression of CD40L on peripheral blood lymphocytes derived from normal, disease control, and SLE individuals. "Disease control" patients include those with seropositive rheumatoid arthritis, progressive systemic sclerosis, Reiter's syndrome, and autoimmune thyroid disease.

Figure 1B:
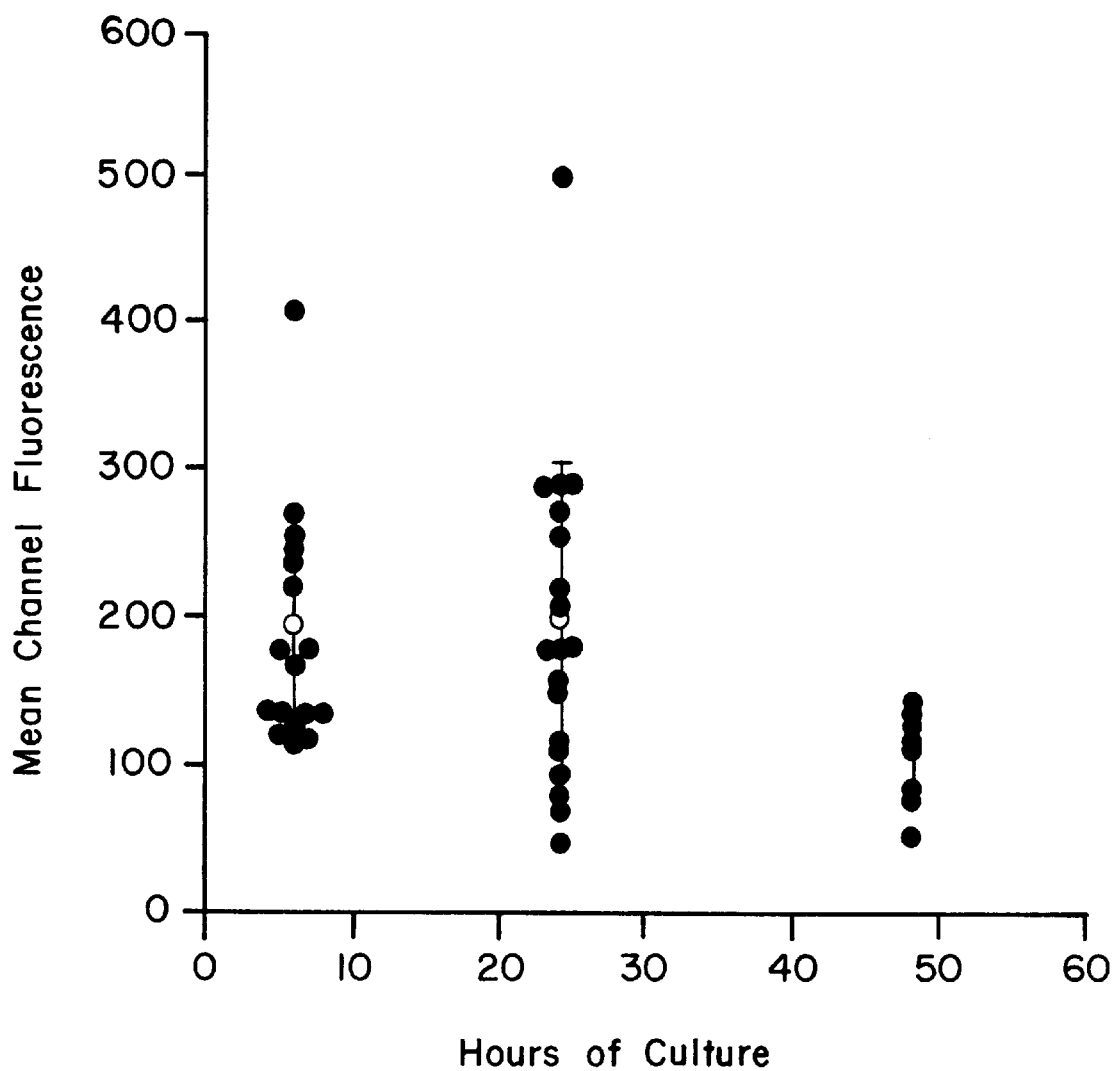
Figure 1C:
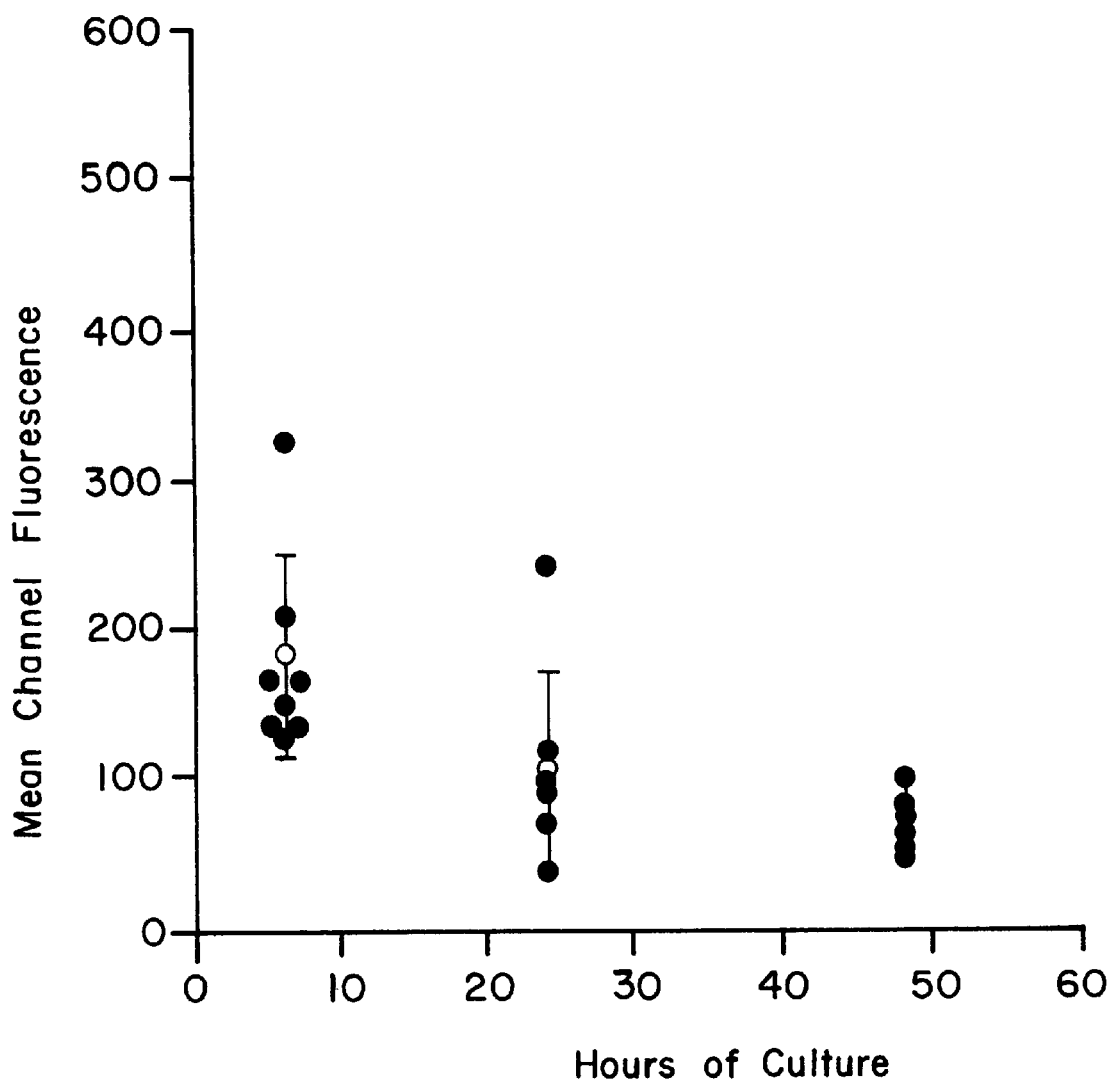

Peripheral blood mononuclear cells (PBMC) isolated by Ficoll-hypaque were cultured for 6, 24, or 48 hours in the presence of 5 ng/ml of the phorbol ester (PMA) and 500 ng/ml ionomycin, after which they were stained with anti-CD40L antibody and a fluorescent second antibody. CD40L levels were quantified by flow cytometry and expressed as the mean channel fluorescence (MCF) of the population of gated cells above the upper limit of the background fluorescence (FIGS. 1A, 1B and 1C). As a control, CD25 (Tac) expression was quantified in parallel.

Figure 2:
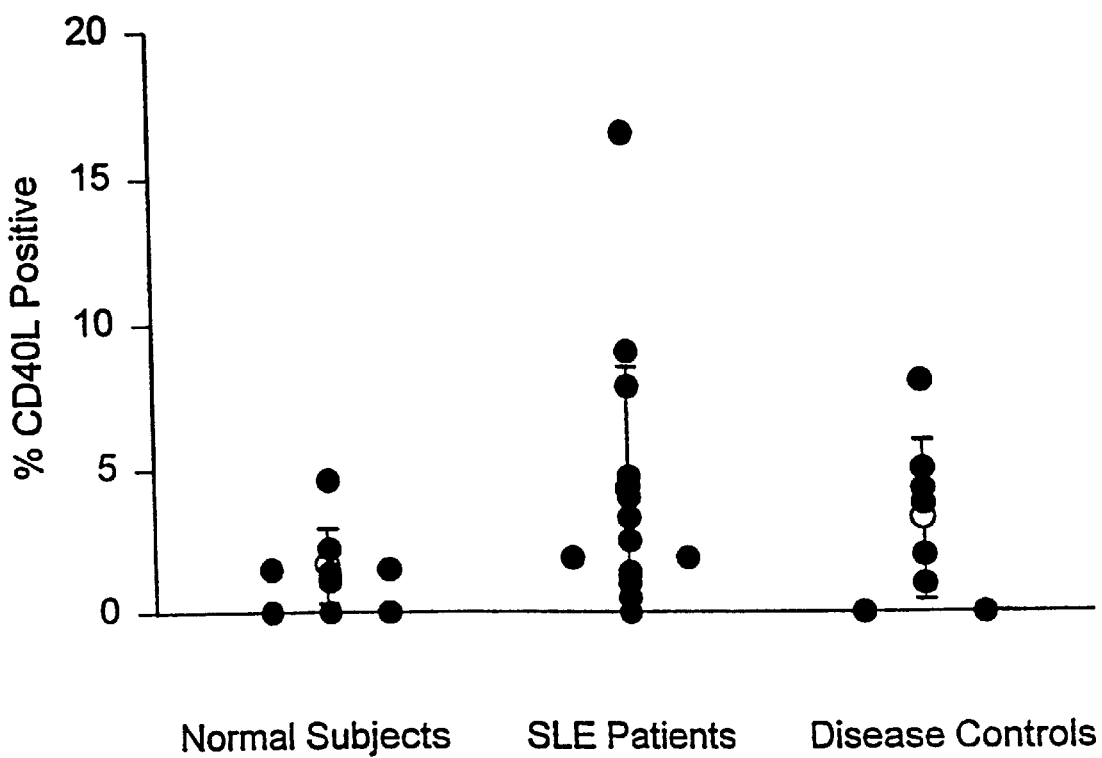
FIG. 2 is a histogram showing CD40L expression on peripheral blood lymphocytes in the absence of activation. Results are expressed as the percentage of CD40L-positive cells after subtraction of background.
Figure 3A:
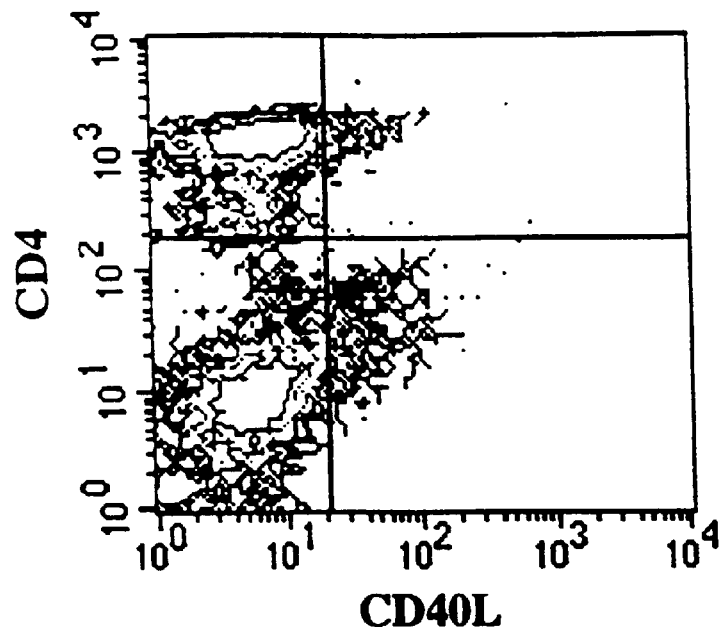
FIGS. 3A–3H are graphic illustrations of CD40L expression on untreated CD4-positive normal and SLE T-cells. Cells were analyzed by multiparameter flow cytometry after a 6 h incubation with medium alone or with the phorbol ester (PMA) and ionomycin. The left panels show Cd4 expression on the Y axis and CD40L expression on the X axis. The right panels show histograms indicating the fluorescence intensity on the Cd4-positive T-cells.
Figure 3B:
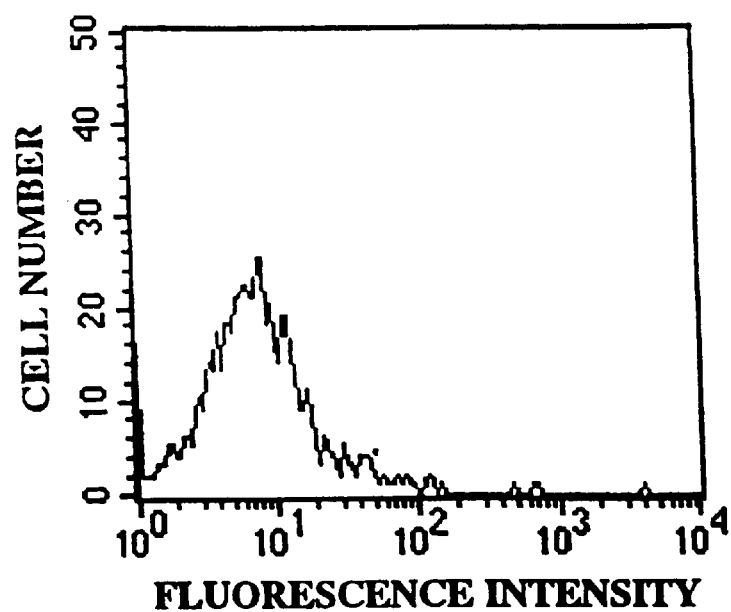
Figure 3C:
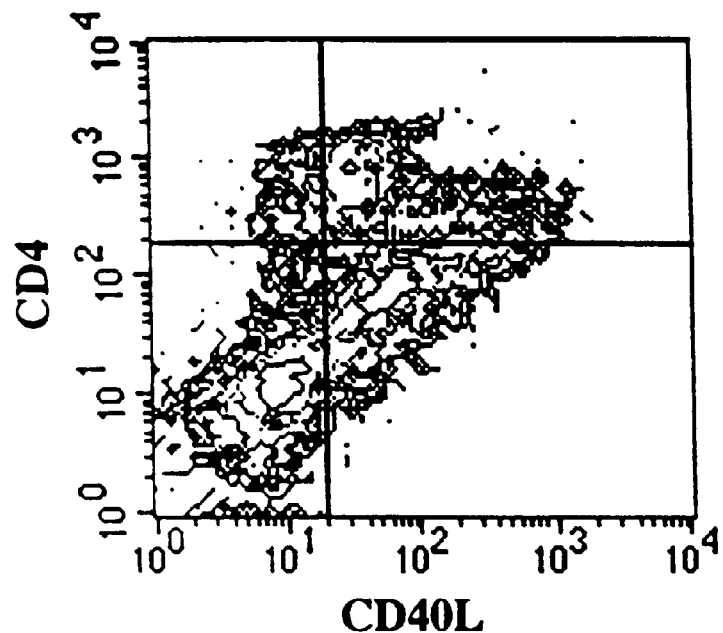
Figure 3D:
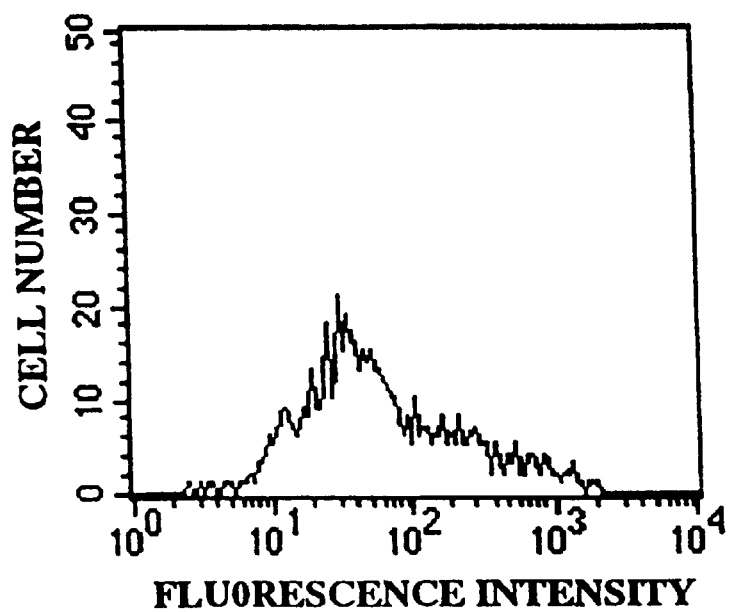
Figure 3E:
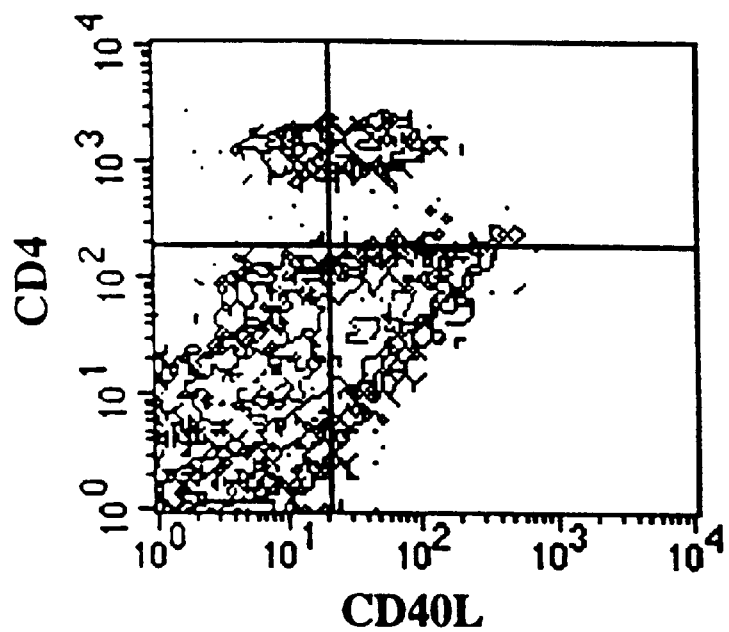
Figure 3F:
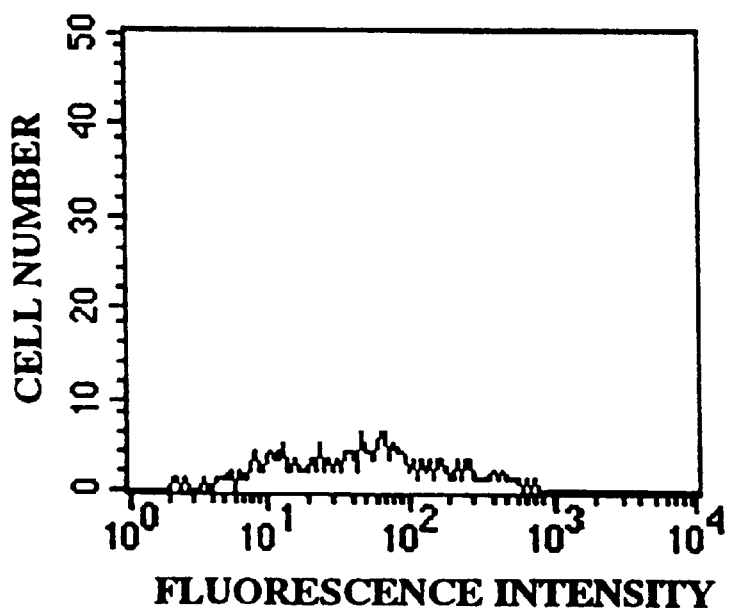
Figure 3G:
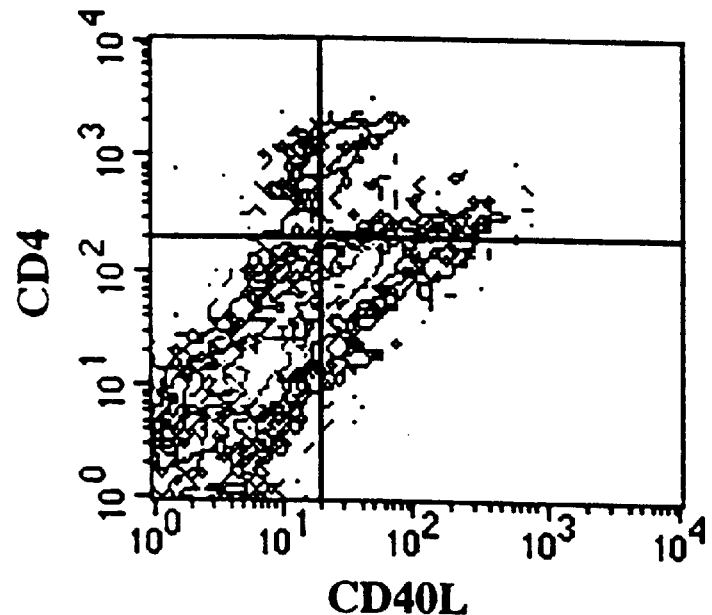
Figure 3H:
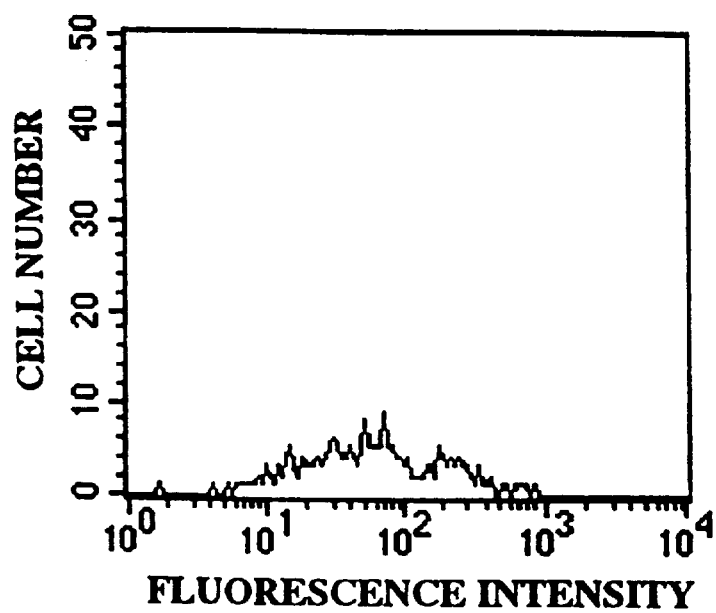
Figures 4B, 4D, 4F:
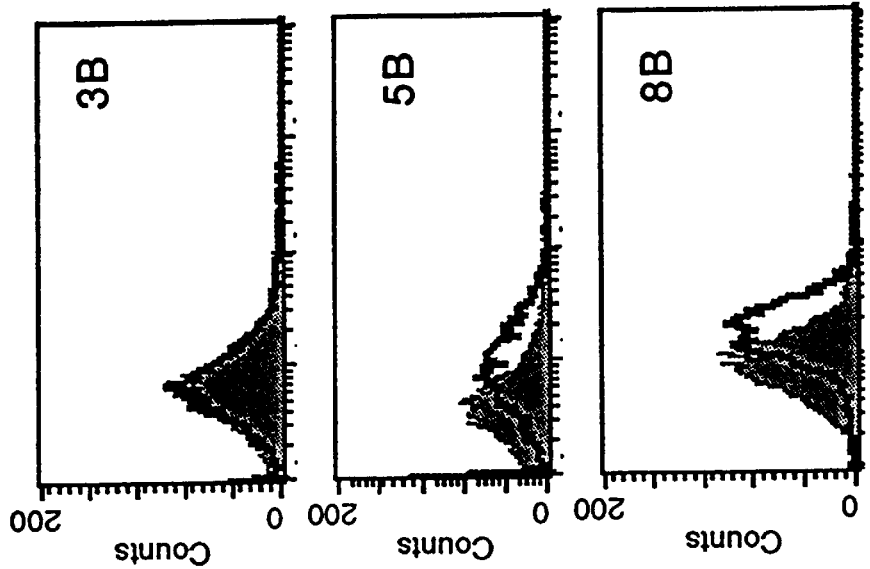
FIGS. 4A–4L are graphic illustrations of fluorescence-activated cell sorting (FACS) analysis of CD40L expression on purified B cells that were obtained from 12 different patients suffering from chronic lymphocytic leukemia (CLL). CD40L expression is indicated by the black line. Background immunofluorescence, defined using an irrelevant monoclonal antibody, is shown by the shaded area.
Figures 4A, 4C, 4E:
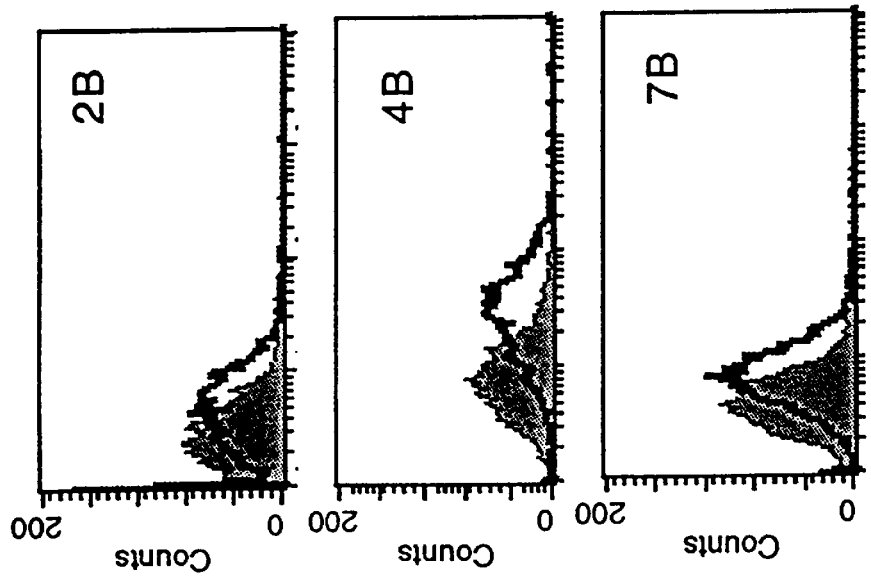
Figure 4G:
Figure 4I:
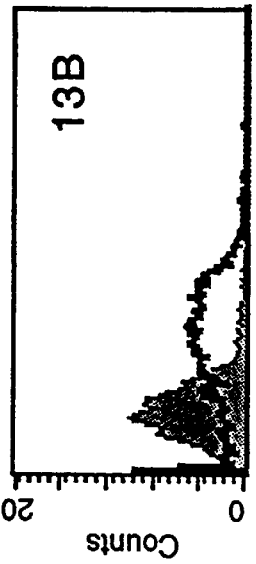
Figure 4K:
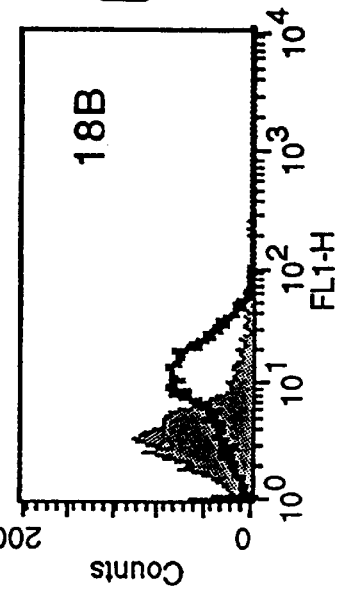
Figure 4H:
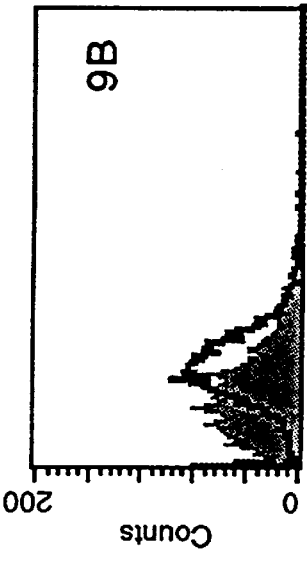
Figure 4J:
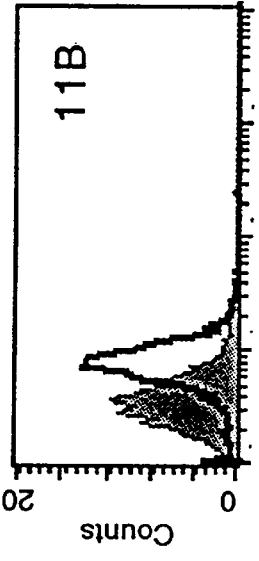
Figure 4L:
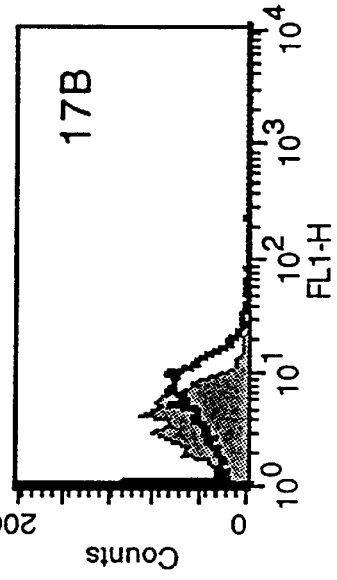

While activated cell populations from healthy subjects (n=14) and disease control patients (n=8) show maximal MCF of CD40L after 6 h of culture, with a gradual decrease to near baseline levels at 48 h of culture, activated lymphocytes from SLE patients (n=19) continue to demonstrate high CD40L levels at 24 and 48 h (p=0.01 and 0.038 at 24 h, respectively, when compared with normal subjects, and p=0.035 and 0.042 at 24 and 48 h, respectively, when compared with disease controls). By contrast, the kinetics and absolute levels of CD25 expression were comparable in normal control and SLE cells, with the MCF gradually increasing over 48 h of culture. Notably, expression of CD40L on untreated PBMC was increased in some of the SLE patients (FIG. 2). Three of the SLE patients with the highest baseline expression of CD40L had renal disease, suggesting that this phenomenon is related to disease activity. Multiparameter fluorescence analysis showed CD40L on untreated CD4+ T cells (FIGS. 3A–3H).

These data indicate that both SLE and normal T helper cells rapidly express high levels of CD40L in response to activation by PMA and ionomycin. In normal subjects, CD40L is quickly downregulated and nearly gone from the cell surface by 48 h; in SLE patients, by contrast, T cells show prolonged high level expression of CD40L for more than 24 h. In addition, lymphocytes from patients with active SLE express some CD40L even in the absence of in vitro activation.

EXAMPLE 2

Increased expression of CD40L in Patients with Chronic Lymphocytic Leukemia

The following experiments were performed to examine the level of expression of CD40L on purified peripheral blood B lymphocytes derived from individuals suffering from CLL.

Peripheral blood B cells were purified from whole blood by Ficoll-Hypaque and T cells were removed from the preparation by rosetting with sheep red blood cells. CD40L levels were quantified by flow cytometry as described in Example 1. As a control, the cells were stained with an irrelevant isotype matched monoclonal antibody to the human TCRVβ13 chain.

The results are shown in FIGS. 4A–4L. The CD40L pattern is indicated by the thick black line, while the control pattern is indicated by the shaded grey area. The results indicate that the B cells from 11 of 12 patients with CLL exhibit higher than control expression of CD40L.

EXAMPLE 3

Detection of Soluble CD40L by ELISA

The method described below is used to measure sCD40L in samples comprising human serum or other body fluid.

A. Elisa Protocol 1. 96-well microwell plates are coated with a mouse monclonal anti-human CD40L antibody (Pharmingen, San Diego, Calif.). 50 µl of the antibody at a final concentration of 1 ng/µl in 50 mM sodium carbonate buffer is added to each well, and the plate incubated overnight at 4° C. The plate is then washed in phosphate buffered saline containing 0.01% (v/v) Tween-20 (PBS-T), and blocked by incubation with PBS-T containing 10% milk for 2 h at room temperature.

2. 50 µl of the sample to be measured is added to a well, after which the plate is incubated at 37° C. for 4 h or overnight at 4° C. The plate is then washed three times with PBS-T.

3. 50 µl of 1:1000 dilution of alkaline phosphate-conjugated mouse monoclonal anti-human CD40L (Ancell, Bayport Minn.) is then added to each well, after which the plate is incubated at 37° C. for 2 h. The plate is then washed three times with PBS-T.

4. 50 µl of developing substrate (prepared by dissolving two tablets of Sigma 104 phosphate substrate in 10 ml diethanolamine) is added per well and the plate is incubated in the dark at 37° C. for 15 min. The absorbance at 405 nm is then measured in an automated ELISA reader.

B. Samples

1. To generate a standard curve, cytosolic extracts of the D1.1 CD40L-positive Jurkat T-cell line or recombinant human CD40L were added in concentrations ranging from 3–400 pg/ml protein.

2. Negative controls included cytosolic extracts of the B2.7 CD40L-negative Jurkat T-cell line, as well as PBS as a buffer control.

C. Results

Figure 5A:
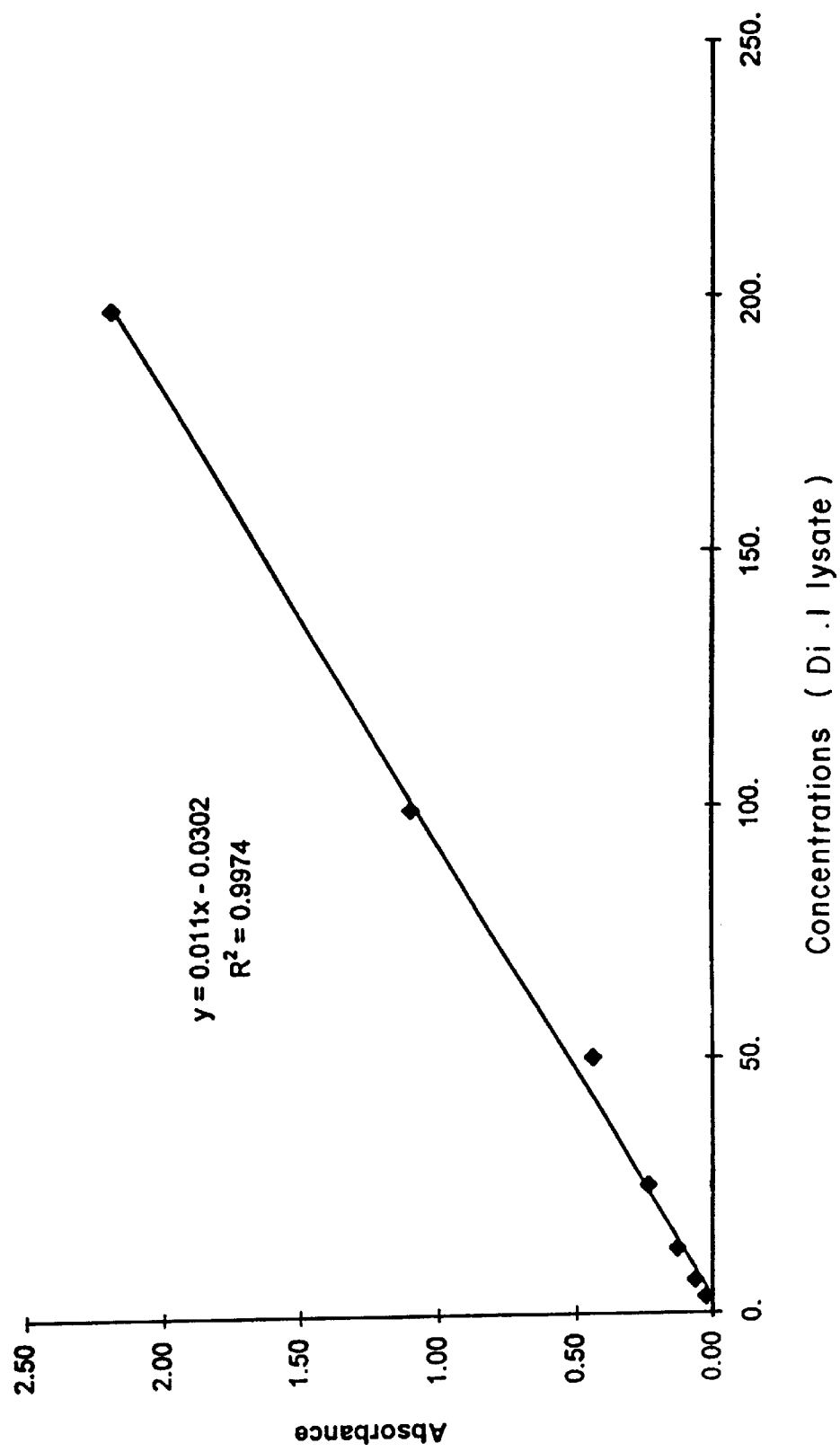
FIGS. 5A–B is a graphic illustration of a standard curve of an ELISA measuring CD40L present in cytosolic extracts derived from D1.1 Jurkat T-cells.
Figure 5B:
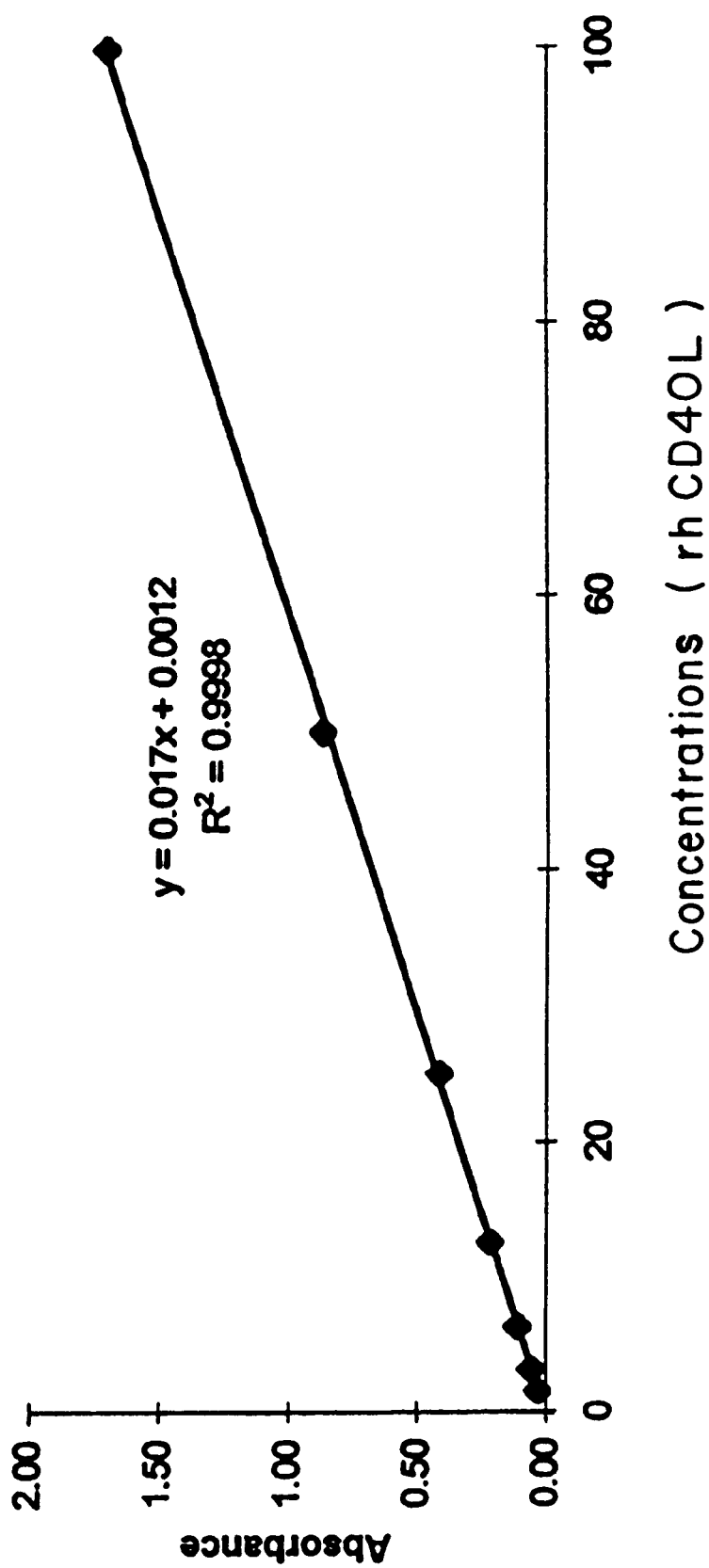
Figure 6A:
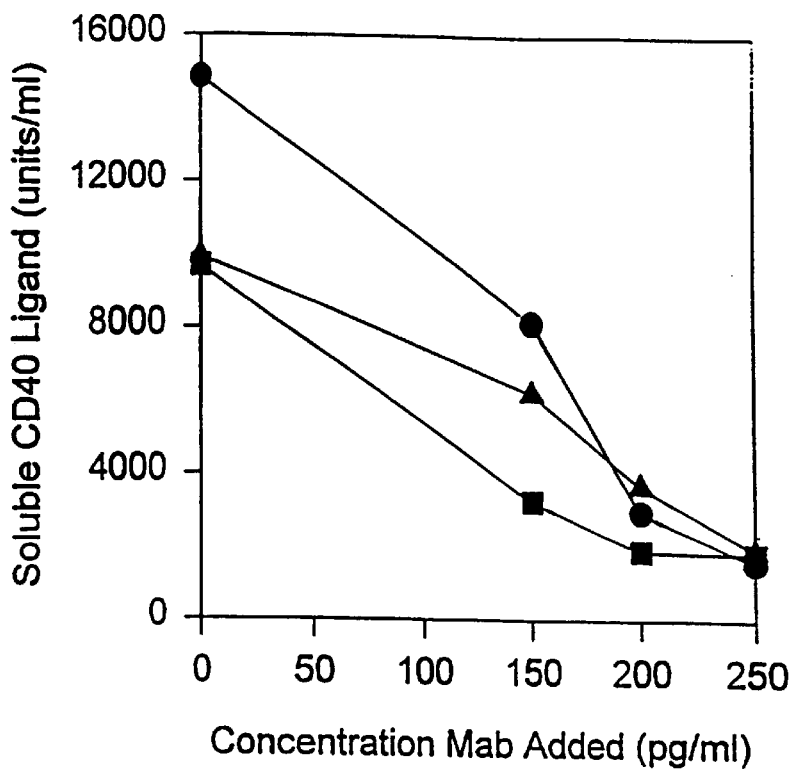
FIGS. 6A–B is a graphic illustration of CD40L levels as measured by ELISA in a cytosolic extract of D1.1 Jurkat T-cells (squares) and in sera from two patients suffering from SLE (triangles and circles). Serum samples were incubated for 16 h with increasing concentrations of anti-CD40L monoclonal antibody prior to the ELISA.
Figure 6B:
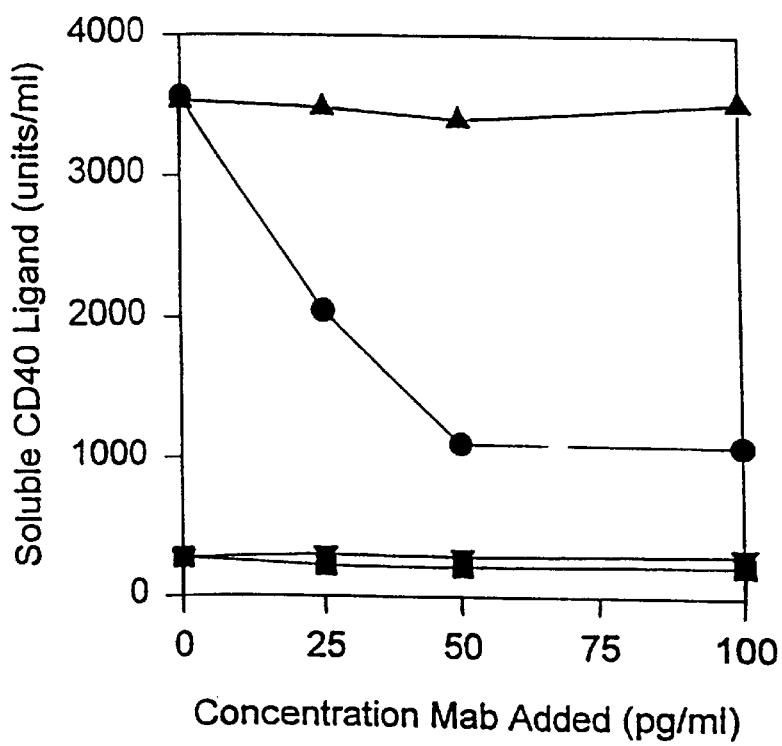

FIGS. 5A and 5B show that the ELISA described above readily detects CD40L in D1.1 cell lysates over a range of concentrations and also detects purified recombinant human CD40L. The specificity of the assay was demonstrated by pre-incubating the D1.1 cell lysate with increasing concentrations of an anti-CD40L monoclonal antibody (FIG. 6A, squares), which reduced the detection of sCD40L by the assay. Similar pre-incubation of sera from two patients with SLE also reduced the detection of sCD40L (FIG. 6A, triangles and circles). Incubation of SLE serum with an irrelevant antibody (anti-CD71), by contrast, had no effect on CD40L detection by the assay (FIG. 6B).

EXAMPLE 4

Increased Soluble CD40L in Serum from SLE Patients

Serum samples were collected from healthy ("normal") subjects; "disease controls" (including patients suffering from rheumatoid arthritis, anti-phospholipid syndrome, Lyme disease, and osteoarthritis); patients with systemic vasculitis (including polyarteritis nodosa, Wegener's granulomatosis, and hepatitis B and C-related vasculitis); and patients with SLE, including active and inactive SLE. (SLE was deemed active if renal involvement, central nervous system disease was documented). Serum sCD40L levels were then measured using the ELISA described in Example 3 above.

Figure 7:
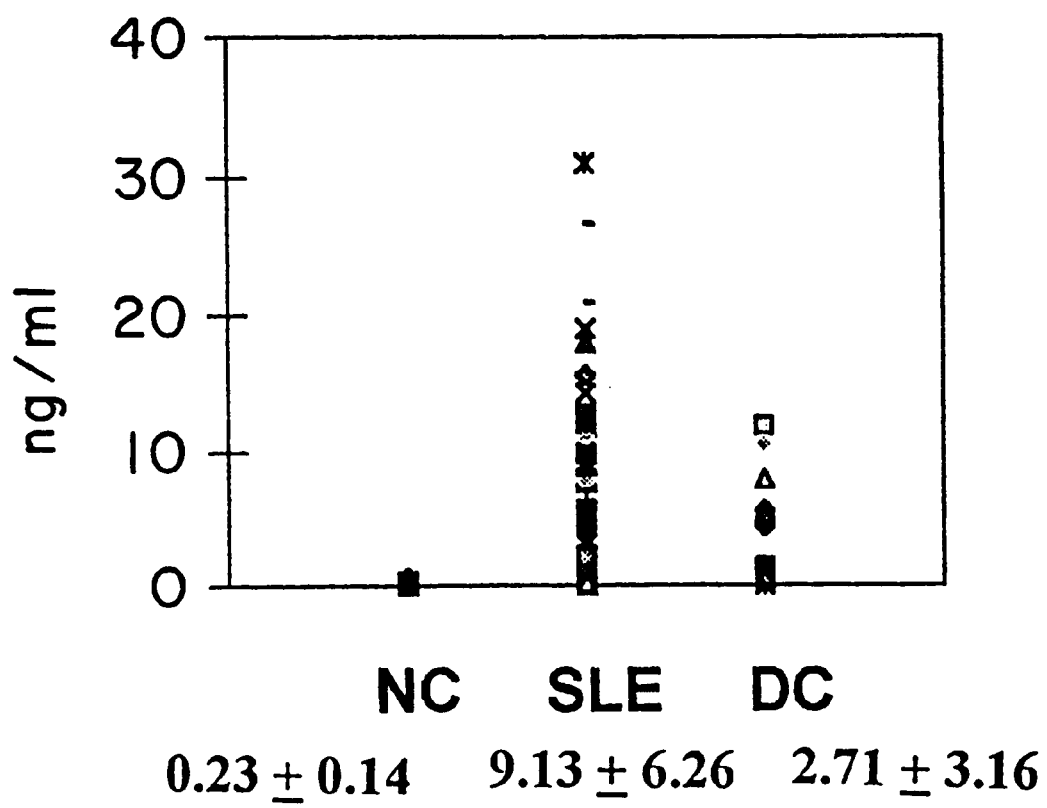
FIG. 7 is a graphic illustration of CD40L levels, as measured by ELISA, in serum samples obtained from patients suffering from SLE, inflammatory diseases (disease controls, DC), or healthy subjects (NC).
Figure 9:
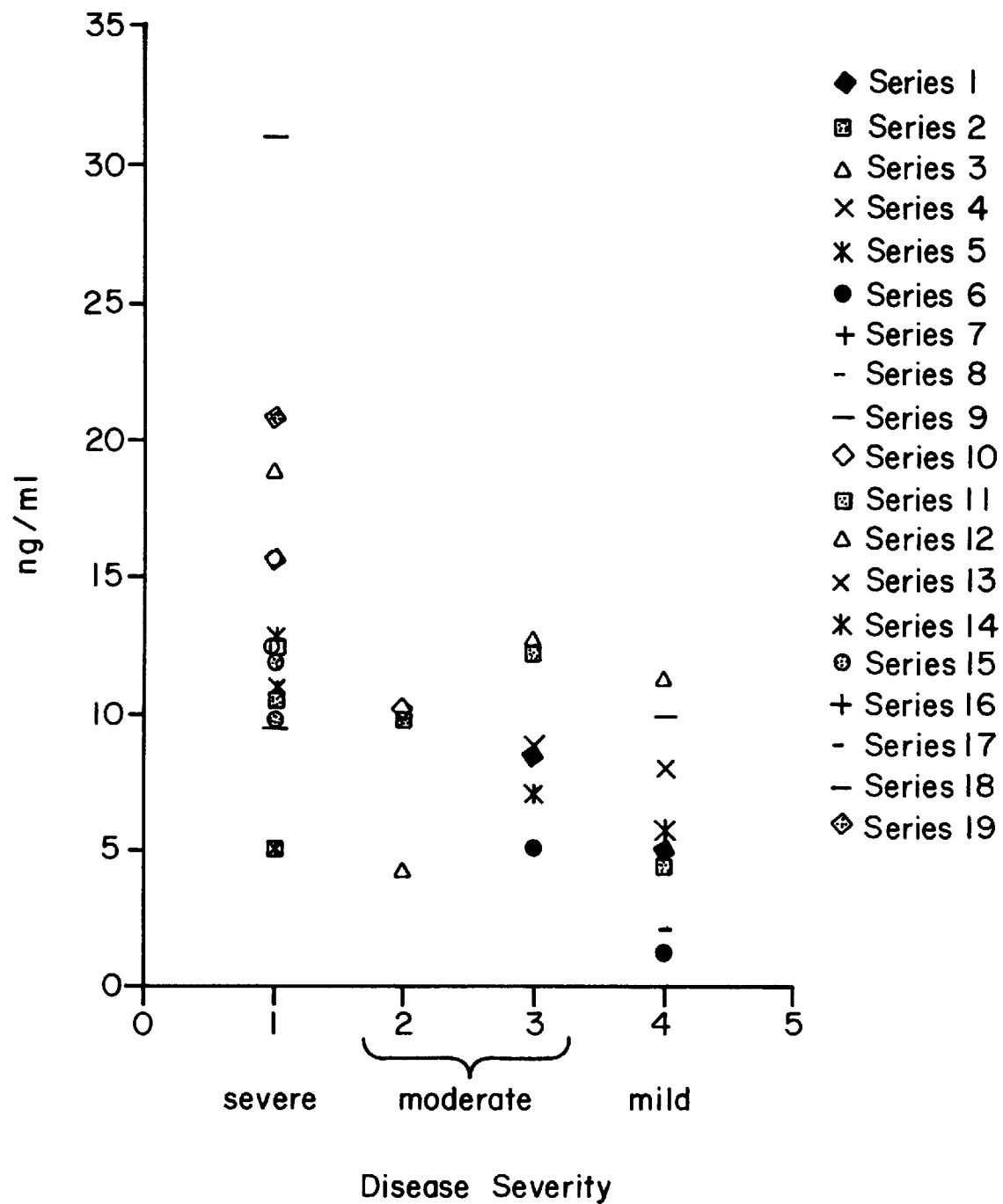
FIG. 9 is a graphic illustration of serum concentrations of soluble CD40L in serum from SLE patients with severe disease, patients with moderate disease, and SLE patients with mild disease.

The results indicate that the distribution of serum sCD40L levels differs significantly among the different patient groups. Serum sCD40L levels in SLE patients were significantly increased relative to controls, ranging from 1000–30,000 pg/ml (FIG. 7 and FIG. 8A). Furthermore, serum sCD40L levels were significantly higher in patients with active SLE than those with inactive SLE (FIG. 8B and FIG. 9).

These data demonstrate that the levels of sCD40L in the serum of patients can serve as a useful diagnostic indicator of SLE disease activity.

EXAMPLE 5

Demonstration of Soluble CD40L in Sera from SLE Patients by Immunoblotting

The following experiments were designed to demonstrate the use of immunoblotting to determine the amount and molecular mass of soluble CD40L in serum. Sera from patients with SLE were subjected to immunoprecipitation with anti-CD40L monoclonal antibody, after which the immune complexes separated by electrophoresis and transferred to a membrane. Soluble CD40L was visualized by immunobloting using as a primary antibody rabbit anti-CD40L antiserum. Bound antibody was detected using a chemiluminesence kit.

Figure 10:
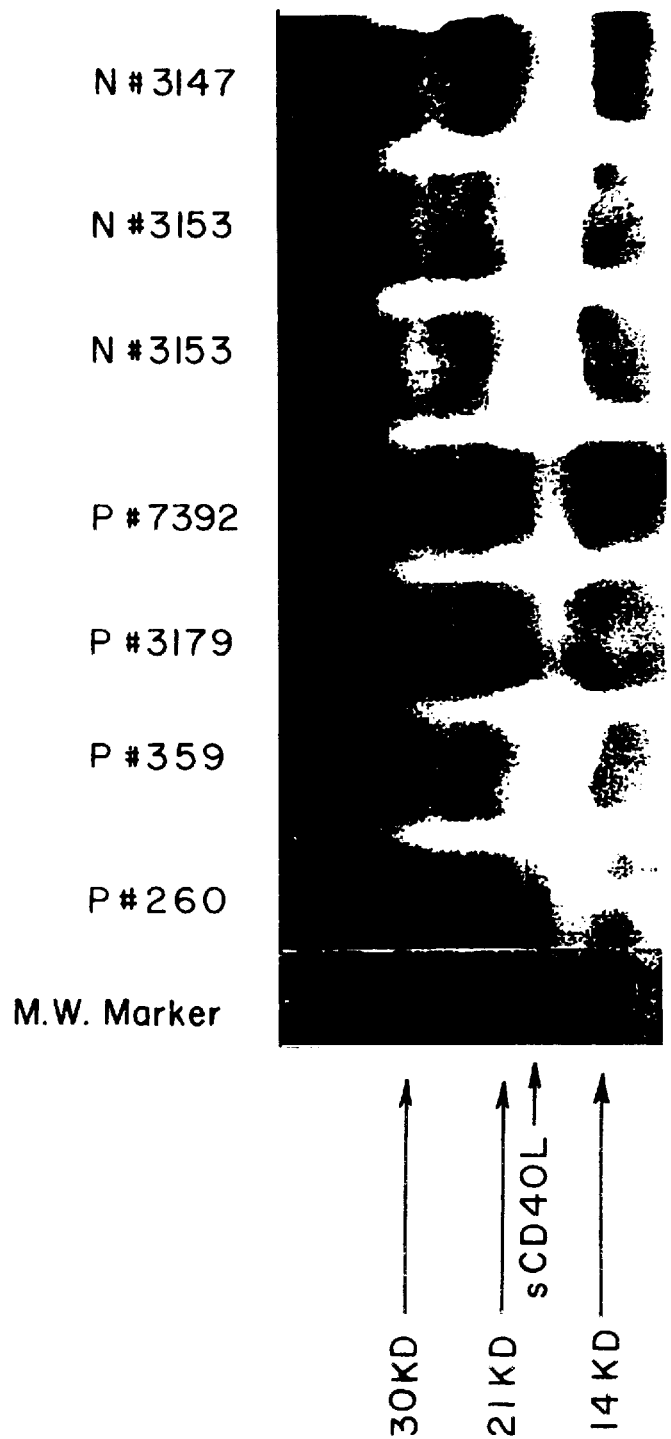
FIG. 10 is a photographic illustration of an immunoblot showing the detection of a soluble CD40L in serum from 3 of 4 patients with SLE or inflammatory disease. The 18 KDa band corresponding to sCD40L was visualized using a rabbit anti-CD40L antiserum.

The results indicated that a protein species having a molecular mass of 18 kDa, corresponding to soluble CD40L, could be detected in serum from 3 of 4 patients with SLE or inflammatory disease (FIG. 10). No 18 kDa species, however, was detected in sera from 3 normal subjects.

EXAMPLE 6

Soluble CD40L Induces Expression of Activation Antigens on B Cells

The experiments described below were performed to determine whether soluble CD40L induces expression of activation antigens, such as, e.g., the Fas antigen, on target cells. Ramos B cells, derived from a patient with Burkitt's lymphoma, were incubated for 48 hours with culture medium alone, with supernatant from 293 cells expressing CD40L, or with supernatant from 293 cells expressing CD8. Fas (CD95) expression was measured on the Ramos B cells by flow cytometry using a fluorescein-labeled anti-CD40L antibody.

Figure 11A:
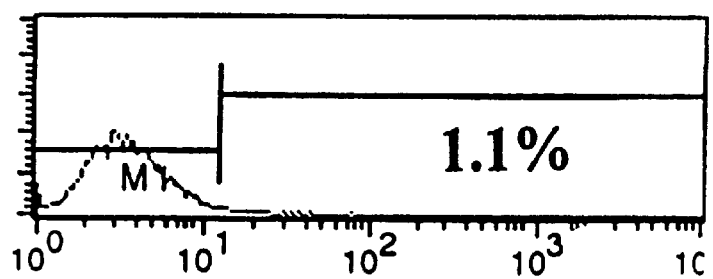
FIGS. 11A–C are graphic illustrations of FACS analysis of the induction of Fas (CD95) expression by sCD40L. Ramos B cells derived from a patient with Burkitt's lymphoma were incubated for 48 hours with culture medium alone ("medium"), with supernatant from 293 cells transfected with CD40L ("293-CD40L"), or with supernatant from 293 cells expressing CD8 ("293-CD8"). Fas expression was measured by direct immunofluorescence using a fluorescein-labeled anti-Fas antibody. The percentage of cells that were determined to be Fas-positive is indicated on each histogram.
Figure 11B:
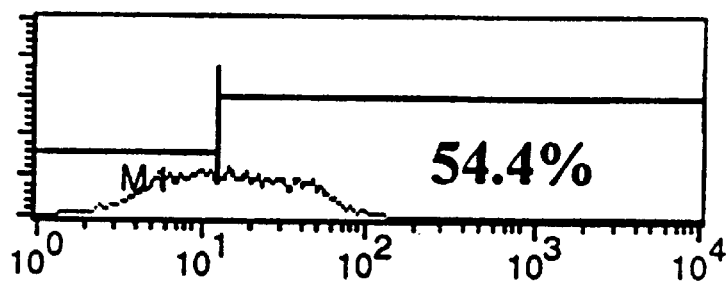
Figure 11C:
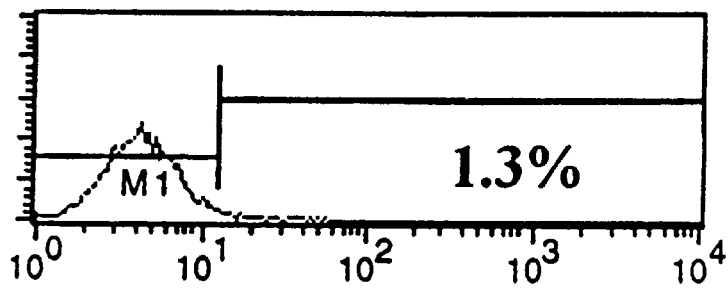
Figure 11D:
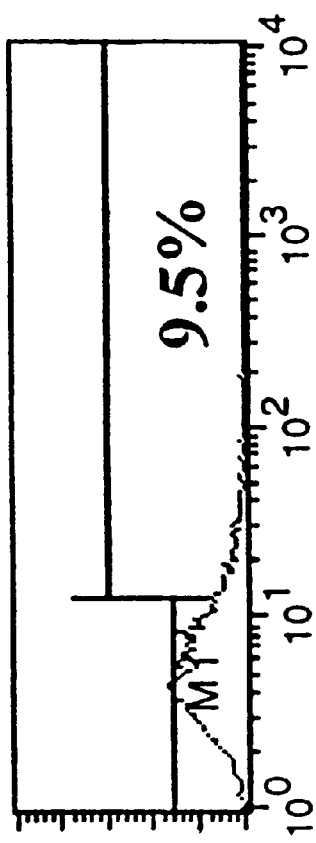
FIGS. 11D–11H are graphic illustrations of FACS analysis demonstrating a dose response of Fas expression on Ramos B cell line cells cultured for 48 hours with varying concentrations of recombinant human CD40L. The concentrations of recombinant CD40L that increased Fas expression are in the range observed in sera of partients with systemic autoimmune and inflammatory diseases. The percentage of cells that were determined to be Fas positive is indicated on each histogram.
Figure 11E:
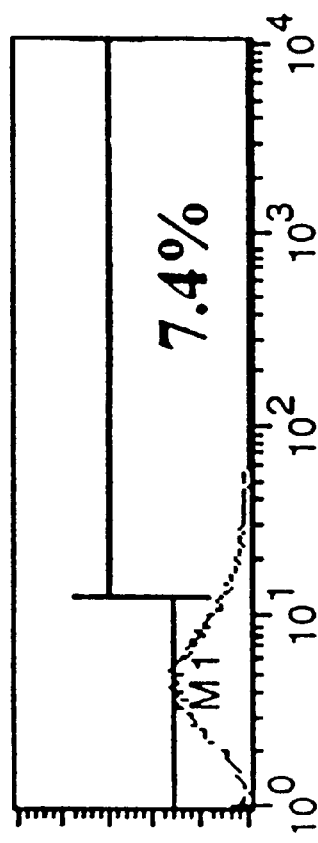
Figure 11F:
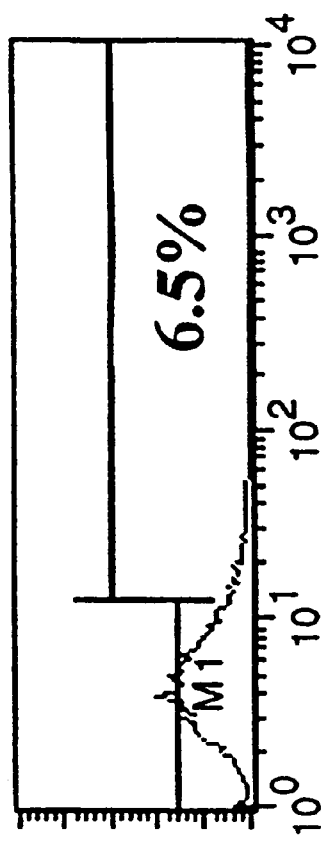
Figure 11G:
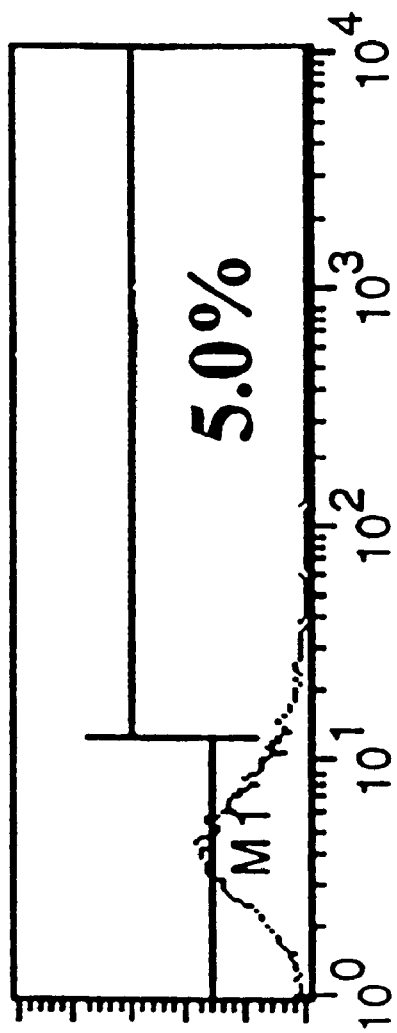
Figure 11H:
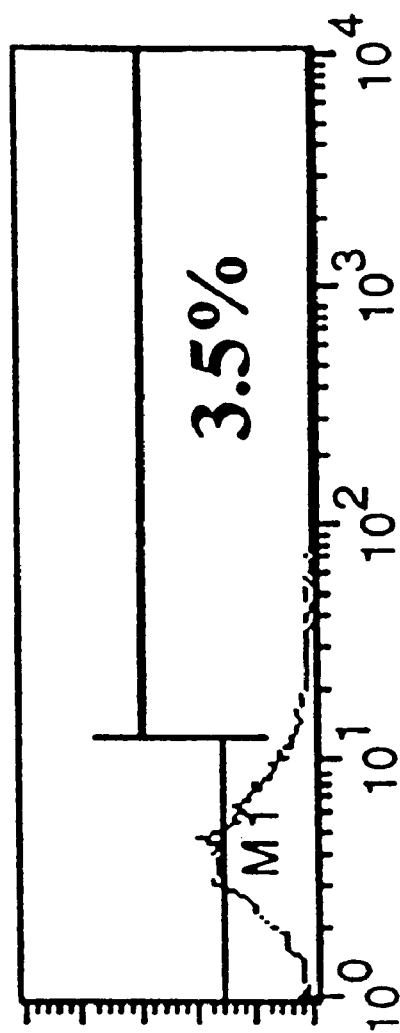

The results indicated that incubation with supernatant from CD40L expressing cells increased the expression of Fas antigen on the target cells (FIGS. 11A–11C). Furthermore, purified recombinant CD40L was shown to increase Fas expression in a dose-dependent manner (FIGS. 11D–11H).

EXAMPLE 7

Correlation of Serum sCD40L Levels and Response to Immunosuppressive Therapy

The following experiment were performed to evaluate the possible relationship between serum sCD40L levels and response to immunosuppressive therapy.

Serum samples were obtained from nine patients suffering from chronic renal disease (i) before initiation of cyclosporin A treatment and (ii) five days after initiation of cyclosporin-A treatment at 10–14 mg/kg/day. Serum sCD40L levels were measured using ELISA as described in Example 3 above.

Figure 12:
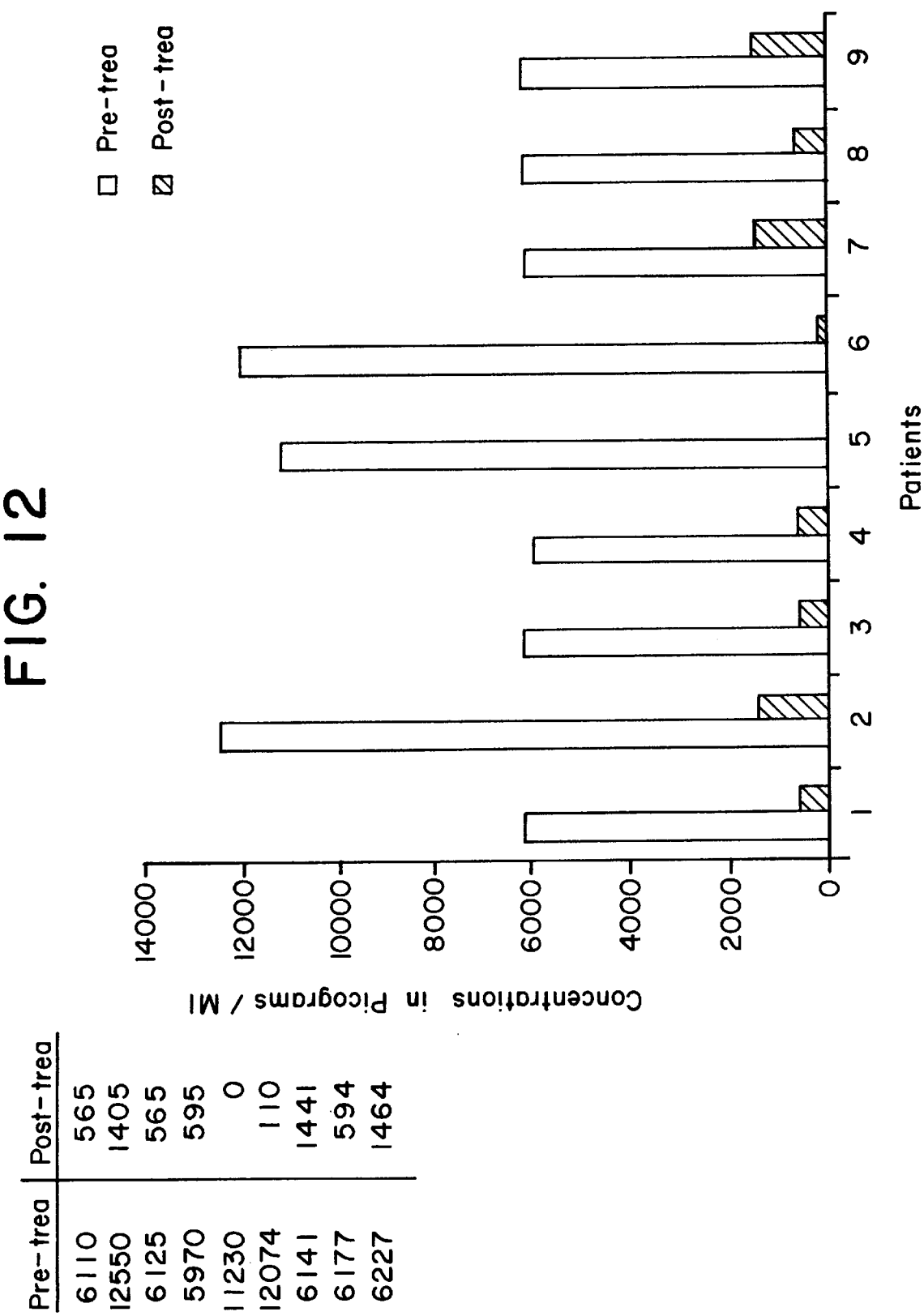
FIG. 12 is a graphic illustration of CD40L levels, as measured by ELISA, in the sera of nine patients suffering from chronic renal disease. Serum samples were obtained before initiation of treatment with cyclosporin A and five days subsequently.

The results demonstrate that serum sCD40L levels decreased markedly in all of the patients subsequent to cyclosporin A treatment (FIG. 12). These data indicate that serum sCD40L levels can serve as a useful diagnostic indicator of the efficacy of immunosuppressive therapies.

What is claimed is:

1. A method for determining a level of disease activity in a patient previously diagnosed with systemic lupus erythematosus (SLE), comprising (i) measuring sCD40L in body fluid collected from the SLE patient and a population of normal control patients, wherein said measuring is achieved using a method selected from the group consisting of immunoassay, receptor-binding assay, and biological activity assay; and (ii) correlating the level of sCD40L measured in the body fluid collected from the SLE patient with the level of SLE disease activity in the patient, wherein active disease is characterized by the presence of about 5,000 to about 30,000 pg sCD40L/ml body fluid, inactive disease is characterized by the presence of 1,000 to below about 5,000 pg sCD40L/ml body fluid and no disease is characterized by the mean level of sCD40L in the population of normal control patients.

2. The method of claim 1, wherein the level of active disease comprises:

(a) severe disease characterized by a level of sCD40L of 12090±6940 pg sCD40L/ml body fluid;

(b) moderate disease characterized by a level of sCD40L of 7930±3860 pg sCD40L/ml body fluid; or (c) mild disease characterized by a level of sCD40L of 5280±3900 pg sCD40L/ml body fluid.

3. A method as defined in claim 1, wherein said body fluid is selected from the group consisting of plasma serum, urine, saliva, synovial fluid, and cerebrospinal fluid.

* * * * *